United States Patent [19]

Bonte et al.

[11] Patent Number: 5,514,374
[45] Date of Patent: May 7, 1996

[54] COSMETIC OR PHARMACEUTICAL COMPOSITION CONTAINING A BLACK HOREHOUND EXTRACT

[75] Inventors: Frédéric Bonte; Alain Meybeck, both of Courbevoie; Marc Dumas, Colombes, all of France

[73] Assignee: L.V.M.H. Recherche, Colombes Cedex, France

[21] Appl. No.: 244,582

[22] PCT Filed: Nov. 27, 1992

[86] PCT No.: PCT/FR92/01105

§ 371 Date: May 27, 1994

§ 102(e) Date: May 27, 1994

[87] PCT Pub. No.: WO93/10804

PCT Pub. Date: Jun. 10, 1993

[30] Foreign Application Priority Data

Nov. 29, 1991 [FR] France ................................ 91 14849

[51] Int. Cl.$^6$ ........................... A61K 35/78; A61K 7/021

[52] U.S. Cl. .................... 424/195.1; 424/63; 424/70.6; 424/78.03; 514/558

[58] Field of Search .................... 424/695.1, 78.03, 424/70.6, 63; 514/558

[56] References Cited

PUBLICATIONS

Chem. Absts. 91(11)91790a, 1979.

*Primary Examiner*—John W. Rollins
*Attorney, Agent, or Firm*—Beveridge, DeGrandi, Weilacher & Young

[57] ABSTRACT

A black horehound extract is used to prepare a cosmetic or pharmaceutical composition, particularly a dermatological composition, for promoting skin pigmentation, preventing or delaying the growth of grey hairs, treating pigmentary disorders, reducing triglyceride levels in fat cells, and preventing the build-up of body fat such as in cellulite. The composition may particularly be used effectively to promote skin or hair pigmentation and a reduction in the build-up of body fat such as in cellulite.

62 Claims, No Drawings

COSMETIC OR PHARMACEUTICAL COMPOSITION CONTAINING A BLACK HOREHOUND EXTRACT

The present invention relates essentially to a cosmetic or pharmaceutical composition, especially dermatological composition, containing an extract of black horehound, intended in particular for promoting the pigmentation of the skin or hair or for reducing the amount of triglycerides in the adipocytes, and to the process for its manufacture.

The present invention further relates to the use of an extract of black horehound for the preparation of such a cosmetic or pharmaceutical composition intended in particular for treating pigmentation disorders or for reducing the amount of triglycerides in the adipocytes.

The plants of the genus Ballota belong to the family of the Labiatae, which are found in temperate regions. An example which may be mentioned is Ballota nigra (LINN.) or Ballota foetida, also known as black horehound. This is a common perennial plant which is found particularly in uncultivated places, along hedges, paths or walls. It has a most unpleasant smell. Other examples which may be mentioned are Ballota lanata, which is cultivated in gardens, and Ballota suavelens or odoriferous ballota, which is recommended as an emmenagogue and antihysteric.

Black horehound is traditionally said to possess tonic, stomachic, antispasmodic, calming, depurative, diuretic, anthelmintic, resolvent and detersive properties.

The present invention is based on the discovery that extracts of black horehound originating from the whole plant, and especially from the aerial parts and in particular the stems and leaves, have valuable biological properties which can be used in the fields of 05 cosmetics and pharmaceutics. The inventors have observed in particular that these extracts unexpectedly possess a melanogenesis-stimulating activity on the melanocytes present in the skin or the hair follicles, especially those on the scalp, and thus make it possible to promote the pigmentation of the skin or hair and to treat pigmentation disorders of the skin and hair by promoting more particularly the biosynthesis of melanin. Very good results in this field have been obtained with extracts of the whole plant, and especially of the aerial parts and in particular the stems and leaves of black horehound.

The inventors have also observed that the abovementioned extracts of black horehound are unexpectedly active in reducing the amount of triglycerides in the adipocytes, especially by inhibiting their synthesis in these cells. These extracts thus make it possible to prevent the development of accumulations of fat in the organism, such as cellulitis, so they are particularly useful for the preparation of cosmetic or pharmaceutical slimming compositions, especially dermatological slimming compositions.

One object of the present invention is therefore to solve the new technical problem which consists in providing a novel cosmetic or pharmaceutical composition, especially dermatological composition, intended in particular for promoting the pigmentation of the skin and for preventing or slowing down the appearance of white hair.

A further object of the present invention is to solve the new technical problem which consists in preparing a novel formulation of a cosmetic or pharmaceutical composition which has a good melanogenesis-stimulating activity on the melanocytes present in the skin or the hair follicles, especially those on the scalp.

A further object of the present invention is to provide a solution to the new technical problem which consists in providing a particularly easily obtainable plant extract which in itself has a good melanogenesis-stimulating activity on the melanocytes present in the skin or the hair follicles, without it being necessary to isolate an active substance of any kind, these isolation processes generally being lengthy and expensive.

A further object of the present invention is to solve the new technical problem which consists in preparing a novel formulation of a cosmetic or pharmaceutical composition which is active in reducing the amount of triglycerides in the adipocytes, thereby making it possible to prevent the development of accumulations of fat in the organism, such as cellulitis.

A further object of the present invention is to provide a solution to the new technical problem which consists in providing a particularly easily obtainable plant extract which in itself is active in reducing the amount of triglycerides in the adipocytes, without it being necessary to isolate an active substance of any kind, these isolation processes generally being lengthy and expensive.

All these new technical problems are solved for the first time by the present invention in a satisfactory manner which can be used on the industrial scale.

Thus, according to a first feature, the present invention relates to a cosmetic or pharmaceutical composition, especially dermatological composition, intended in particular for promoting the pigmentation of the skin, for preventing or slowing down the appearance of white hair, for reducing the amount of triglycerides in the adipocytes and for preventing the development of the accumulation of fat in the organism, such as cellulitis, said composition comprising as the active ingredient a cosmetically or pharmaceutically effective amount of an extract of black horehound, optionally in a cosmetically or pharmaceutically acceptable excipient.

In the present description and the claims, "cosmetically or pharmaceutically effective amount" is understood as meaning an amount at least equal to the minimum amount which is necessary for observing a significant cosmetic or pharmaceutical effect.

The extract of black horehound is advantageously selected from extracts of Ballota nigra, Ballota lanata and Ballota suavelens.

According to one particular characteristic of the invention, the extract of black horehound is selected from an extract of the whole plant and an extract of the aerial parts, and essentially the stems and leaves in particular.

According to another characteristic, the abovementioned extract of black horehound is an extract which is advantageously obtained by a process comprising at least one extraction step with, for example, a solvent selected from the group consisting of water, alcohols preferably containing from 1 to 4 carbon atoms, such as methanol, ethanol or propanol, a mixture of these alcohols with water, chlorinated solvents containing 1 or 2 carbon atoms, such as chloroform or dichloromethane, and organic esters preferably containing 3 to 6 carbon atoms, such as ethyl acetate. More generally, solvents which can also be used are organic solvents such as aromatic hydrocarbons, especially benzene, toluene or xylene, halogenated aliphatic or aromatic hydrocarbons, dialkyl ethers, dialkyl ketones, alkanols, carboxylic acids and their esters, or other solvents such as dimethylformamide, dioxane, tetrahydrofuran and dimethyl sulfoxide, or else supercritical carbon dioxide gas. The ratio of plant material to extraction agent can be chosen within a wide range, but is generally between 1:5 and 1:20 parts by weight and preferably about 1:10. The extraction is carried out at temperatures between room temperature and the boiling point of the solvent used for the extraction. A valuable extraction technique is the so-called Soxhlet extraction technique.

It is also possible, however, simply to carry out the extraction under reflux at normal atmospheric pressure for 2 to 4 h after the plant material has optionally been allowed to macerate in the cold for 2 to 4 h in the extraction solvent.

When extraction is complete, the phase containing the extract is filtered and then concentrated and/or evaporated to dryness under reduced pressure or by lyophilization.

This gives an extract according to the invention.

In general, the concentration of the extracts used according to the present invention for the preparation of a cosmetic or pharmaceutical composition, expressed by dry weight, is between 0.0001% and 5% by weight, preferably between 0.01% and 0.5% by weight, based on the total weight of the composition.

The cosmetic or pharmaceutical compositions, especially dermatological compositions, according to the present invention can be prepared in forms appropriate for a variety of modes of administration. In particular, they can be presented in a form intended for topical administration to the skin or scalp, such as a cream, a gel, a milk or a lotion, for promoting the pigmentation of the-skin and preventing or slowing down the appearance of white hair.

Thus the cosmetic or pharmaceutical compositions, especially dermatological compositions, according to the invention have various applications in cosmetology or pharmacy, especially in dermatology, in particular when it is desired to restore normal pigmentation or increase this pigmentation.

For example, these compositions can be used as sun products for accelerating or intensifying tanning, which, in addition to the esthetic advantage often sought after, makes it possible to strengthen the natural defenses against ultraviolet radiation by increasing the melanin content of the epidermis. These compositions can also be used in the form of creams, for example, to give the skin a more sunburnt appearance, or else in the form of lotions for preventing or slowing down the appearance of white hair. Furthermore, in dermatology, the compositions according to the present invention can be used as therapeutic agents, either by themselves or in association with other drugs, in particular by topical administration in the treatment of melanocyte dysfunctions.

As far as the action on the melanocytes is concerned, it has been possible to demonstrate that the extracts according to the invention make it possible to favor the differentiation of the melanocytes, i.e. to favor the production of more mature or better differentiated melanosomes in human melanocyte cultures.

One particularly valuable application involves applying these extracts according to the invention in a method of treating melanocytes in culture, especially normal human melanocytes in culture, so as to cause them to acquire maturation properties appropriate for their subsequent use.

In particular, the subsequent use can consist of melanocyte grafts in humans, especially for treating certain pigmentation disorders such as vitiligo.

Furthermore, the cosmetic or pharmaceutical compositions, especially dermatological compositions, according to the invention also have various applications in cosmetology or pharmacy, especially in dermatology and particularly by topical administration, for reducing the amount of triglycerides in the adipocytes. It is known in particular that the synthesis of triglycerides by the adipocytes goes hand in hand with the development of accumulations of fat in the organism, such as cellulitis. Thus the extracts according to the invention have a particularly valuable application in cosmetic or pharmaceutical slimming compositions, especially dermatological slimming compositions, for preventing or treating excesses of fat, in particular cellulitis.

Advantageously, the abovementioned slimming compositions also contain other active substances such as xanthines, in particular caffeine, an extract of ivy (Hedera Hellix) or an extract of Coleus, in particular Coleus forskolii.

Advantageously, the cosmetic or pharmaceutical compositions according to the invention which are intended for topical administration are advantageously formulated with a particular excipient acting as a penetration vector, i.e. an agent which promotes penetration and diffusion in the skin structures in question, such as those commonly used in the fields of cosmetology and dermopharmacy, examples being ethyl alcohol, a glycol, in particular glycerol or propylene glycol, oleic acid, laurocapram or an essential oil, especially menthol or eucalyptol.

In one advantageous embodiment, a cosmetic or pharmaceutical composition according to the invention which is intended more particularly for the pigmentation of the skin or hair also contains a xanthine, in particular 1-methylxanthine, 3-methylxanthine, 3-iso-butylmethylxanthine or theophylline, preferably at a concentration by weight of between 0.001% and 2% and particularly preferably of between 0.01% and 0.5%, based on the total weight of the composition.

In another embodiment, applicable in particular in the context of activating the pigmentation of the skin or hair, a cosmetic or pharmaceutical composition according to the invention also contains tyrosine or a derivative thereof such as glucose tyrosinate or N-malyltyrosine, preferably at a concentration by weight of between 0.001% and 10%, based on the total weight of the composition.

In yet another embodiment, applicable in particular in the context of activating the pigmentation of the hair, a cosmetic or pharmaceutical composition according to the invention also contains an effective concentration of at least one other active substance selected from vitamins, in particular the B vitamins, quinine or derivatives thereof, rubefacients such as methyl nicotinate, a papilla fibroblast culture supernatant as defined in the document EP-A-272 920, keratin hydrolyzates, trace elements such as zinc, selenium and copper, 5-α-reductase inhibitors such as progesterone, cyproterone acetate, minoxidil, azelaic acid and derivatives thereof, a 1,4-methyl-4-azasteroid, in particular 17-β-N,N-diethylcarbamoyl-4-methyl-4-aza-5 -α-androstan-3-one, or else an extract of Serenoa repens.

In yet another embodiment, a cosmetic or pharmaceutical composition according to the invention also contains hydrated lipidic lamellar phases or liposomes, which may or may not incorporate the extract of Ballota nigra defined above.

According to a second feature, the present invention further relates to a process for the manufacture of a cosmetic or pharmaceutical composition, especially dermatological composition, intended in particular for promoting the pigmentation of the skin, for preventing or slowing down the appearance of white hair, for treating pigmentation disorders of the skin or hair, for reducing the amount of triglycerides in the adipocytes and for preventing the development of accumulations of fat in the organism, such as cellulitis, said process comprising the incorporation of at least one extract of black horehound, as defined above, into a cosmetically or pharmaceutically acceptable excipient, vehicle or carrier.

According to a third feature, the invention relates to the use of an extract of black horehound, as defined above, for the preparation of a cosmetic or pharmaceutical composition, especially dermatological composition, intended in particular for promoting the pigmentation of the skin, for preventing or slowing down the appearance of white hair, for treating pigmentation disorders of the skin or hair, for reducing the amount of triglycerides in the adipocytes and for preventing the development of accumulations of fat in the organism, such as cellulitis.

According to yet another feature, the present invention further relates to a cosmetic or therapeutic method of treating a pigmentation insufficiency or pigmentation disorders, said method comprising the application of an effective amount of at least one extract of black horehound, as defined above, advantageously incorporated in a cosmetically or pharmaceutically acceptable excipient, vehicle or carrier, preferably to the affected areas of the skin or scalp of a human being, so as to restore normal pigmentation of the skin or hair and/or increase this pigmentation.

According to yet another feature, the present invention further relates to a method of treating melanocytes in culture, especially human melanocytes in culture, so as to cause them to acquire maturation properties appropriate for subsequent use, said method comprising the cultivation of said melanocytes in a culture medium comprising an effective amount of at least one extract of black horehound for a sufficient period of time to obtain differentiation of the melanocytes.

According to yet another feature, the present invention relates to a cosmetic or therapeutic method of treatment consisting of melanocyte grafts in a mammal, preferably in man, said method comprising the grafting of melanocytes, especially human melanocytes, which have undergone differentiation by culture in the presence of an amount, effective for differentiation, of at least one extract of black horehound, as defined above.

According to yet another feature, the present invention relates to a cosmetic or therapeutic method of treatment for reducing the amount of triglycerides in the adipocytes of a mammal, in particular a human being, said method comprising the application to the areas to be treated, in a preventive or curative capacity, of an amount, effective for reducing the amount of triglycerides in the adipocytes, in particular for inhibiting their synthesis by these cells, of at least one extract of black horehound, as defined above, optionally in a cosmetically or pharmaceutically acceptable excipient, vehicle or carrier.

The invention also covers a method of preventing or treating excesses of fat, in particular cellulitis, said method comprising the application to the areas of the body of a mammal, in particular a human being, suffering from excesses of fat in the organism, such as cellulitis, of an amount, effective for reducing said excesses of fat, of at least one extract of black horehound, as defined above, optionally in a cosmetically or pharmaceutically acceptable excipient, vehicle or carrier.

In all the foregoing features, the extract of black horehound, as defined above, can be used in the presence of hydrated lipidic lamellar phases or liposomes, which may or may not incorporate said extract. It is pointed out that the expression "incorporate" covers the case where the extract is totally incorporated and the case or only a certain amount of this extract is incorporated in the hydrated lipidic lamellar phases or in the liposomes.

The term "lipidic" in the expression "lipidic lamellar phase" covers all substances which comprise a so-called fatty hydrocarbon chain generally containing more than 5 carbon atoms, this substance usually being called a "lipid".

According to the invention, the lipids used to form the lipidic lamellar phases or the liposomes are amphiphilic lipids, i.e. lipids consisting of molecular which possess either an ionic or a non-ionic hydrophilic group and a lipophilic group, these amphiphilic lipids being capable of forming lipidic lamellar phases or liposomes in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an egg or soya lecithin, a phosphatidylserine, a sphyngomyelin, a cerebroside or an oxyethylenated polyglycerol stearate.

It is preferable according to the invention to use a mixture of lipids consisting of at least one amphiphilic lipid and at least one hydrophobic lipid such as a sterol like cholesterol or β-sitosterol. The amount of hydrophobic lipid, expressed in mol, must not generally exceed the amount of amphiphilic lipid and preferably must not be more than 0.5 times this amount.

The compounds or the extracts containing these compounds used according to the present invention can be incorporated into hydrated lipidic lamellar phases or into liposomes by known preparative techniques described for example in the document EP-B1-0 087 993=U.S. Pat. No. 4,508,703, if appropriate in combination with the document EP-B1-0 107 559=U.S. Pat. No. 4,621,023.

Other objects, characteristics and advantages of the invention will become clearly apparent from the following explanatory description referring to several Examples, which are given simply by way of illustration.

In fact, the present invention is in no way limited to the embodiments which have been described and illustrated. Thus, for example, it also covers a cosmetic or dermatological composition intended for preventing or slowing down the graying of the eyebrows or eyelashes.

The percentages are given by weight in the Examples, unless indicated otherwise.

EXAMPLE 1

Preparation of a methanolic extract of black horehound 500 g of aerial parts of Ballota nigra, made up essentially of stems and leaves, are treated under reflux for 3 h with about 5 l of methanol.

The methanolic extracts are filtered and the filtrate is evaporated under reduced pressure and then lyophilized to give a methanolic extract of Ballota nigra called extract $I_1$.

EXAMPLE 2

Preparation of an ethyl acetate extract of black horehound

The procedure described in Example 1 is followed, except that the solvent used is ethyl acetate; this gives an ethyl acetate extract of Ballota nigra called extract $I_2$.

EXAMPLE 3

Incorporation of an extract of whole black horehound plants into hydrated lipidic lamellar phases or into liposomes An extract of whole Ballota nigra plants called extract $I_3$, obtained by following the procedure described in Example 1, except that the whole plants are used, is incorporated into hydrated lipidic lamellar phases or into liposomes by the preparative technique below:

The following are weighed out:
soya lecithin: 1.8 g
β-sitosterol: 0.2 g
lyophilized extract $I_3$ of Ballota nigra: 0.03 g These constituents are dissolved in a mixture consisting of 25 ml of dichloromethane and 10 ml of methanol.

The resulting mixture is evaporated on a rotary evaporator at a temperature of 60° C. under reduced pressure.

The resulting lipidic film is then taken up and dispersed in distilled water qsp 50 g at room temperature for 12 h, with agitation.

The suspension of lipidic vesicles obtained is then homogenized by treatment with ultrasound for 10 min. at 4° C. at a power of 150 W.

The liposomes obtained in this way have a mean size of about 140 nm.

In one advantageous variant, this suspension is then gelled by being mixed with 50 g of 1.25% Carbopol® 940 gel, separately prepared in conventional manner. This gives about 100 g of a gelled suspension of liposomes at least partially encapsulating the extract of black horehound, the concentration of which is about 0.030%, based on the total weight of the suspension.

This gel is called "composition $I_4$" and can be used as such within the framework of the invention.

EXAMPLE 4

Measurement of the efficacy of extracts of black horehound according to the invention on melanocytes in culture
Protocol:

S91 murine melanocytes, inoculated at a rate of $10^5$ cells per dish, are cultivated in EMEM complemented with non-essential amino acids and also containing 1% of fetal calf serum and 0.08 μg/ml of mitomycin C. 24 h after inoculation, the culture medium is replaced with fresh medium containing no mitomycin C and only comprising complemented EMEM, 1% of fetal calf serum and, where appropriate, the test product solubilized in DMSO at a concentration of about 40 mg/ml.

Six days after inoculation, the cells are removed and isolated by centrifugation and the cellular residue is recovered and dissolved in 0.5N sodium hydroxide solution in a sufficient proportion to obtain essentially the same concentration by weight of cells per milliliter of final solution.

The optical density of the solution obtained is read on a spectrophotometer at 405 nm, making it possible to evaluate the amount of melanin formed by comparison with the optical density of a solution of melanin of known concentration.

The cells are also counted and the amount of melanin formed per $10^6$ cells is calculated.

Extracts $I_1$ and $I_2$ of Ballota nigra were tested at various concentrations in micrograms (μg) per milliliter, as also mentioned in Tables I and II below.

In a separate experiment, an equivalent test was carried out to check that the melanocytes used in the present assays gave a positive response to beta-MSH (Melanocyte-Stimulating Hormone).

The melanogenesis-stimulating efficacy E of the test products is calculated by means of the following formula:

$$E = \frac{q_p - q_o}{q_o} \times 100$$

in which the quantities q represent the amounts of melanin formed per $10^6$ cells:

$q_p$: culture receiving the test product $q_o$: control culture receiving no product.

The efficacy E of the extracts tested at different concentrations, calculated by means of the above formula, with:

a) extract $I_1$ of Example 1, or b) with extract $I_2$ of Example 2, is shown respectively in Tables I and II below.

The assays were performed with three dishes per concentration and per product, so the values shown in Tables I and II relating to the number of cells per dish and the amount of melanins, expressed in micrograms (μg) (per $10^6$ cells), are mean values.

A statistical study by the Student t test compares the results of the control cultures with those of the cultures treated with the products according to the invention.

S=significant at 5%,

NS=not significant at 5%.

TABLE I

| Test with extract $I_1$ of Ballota nigra (aerial parts) | | | | |
|---|---|---|---|---|
| Concentration of extract $I_1$ (μg/ml) | Number of cells ± standard deviation per dish × $10^{-3}$ | Melanin, μg per $10^6$ cells | Efficacy E (%) | Significance t |
| 0 (control) | 82 ± 8 | 55 ± 4 | 0 | — |
| 2.5 | 81 ± 2 | 57 ± 4 | +3 | NS |
| 10 | 76 ± 4 | 62 ± 3 | +12 | NS |
| 25 | 77 ± 4 | 66 ± 6 | +20 | S |
| 100 | 75 ± 7 | 71 ± 5 | +29 | S |

TABLE II

| Test with extract $I_2$ of Ballota nigra (aerial parts) | | | | |
|---|---|---|---|---|
| Concentration of extract $I_2$ (μg/ml) | Number of cells ± standard deviation per dish × $10^{-3}$ | Melanin, μg per $10^6$ cells | Efficacy E (%) | Significance t |
| 0 (control) | 80 ± 6 | 53 ± 4 | 0 | — |
| 2.5 | 70 ± 11 | 62 ± 2 | +16 | S |

TABLE II-continued

| | Test with extract $I_2$ of Ballota nigra (aerial parts) | | | |
|---|---|---|---|---|
| Concentration of extract $I_2$ (μg/ml) | Number of cells ± standard deviation per dish × $10^{-3}$ | Melanin, μg per $10^6$ cells | Efficacy E (%) | Significance t |
| 10 | 67 ± 5 | 72 ± 3 | +35 | S |
| 25 | 70 ± 7 | 73 ± 11 | +37 | S |

Tables I and II above show that, at non-cytotoxic doses, the extracts according to the invention stimulate the production of melanin to a significant extent, representing a totally unexpected result for those skilled in the art.

In a separate experiment, it was also demonstrated that the extracts of black horehound according to the invention favor the differentiation of the melanocytes by the formation, within the melanocytes, of a larger number of mature melanosomes transferable to the keratinocytes.

EXAMPLE 5

Demonstration of the activity of the products of the invention on the differentiation of melanocytes in culture The process of pigmentation of the skin's epidermis is known to involve differentiation of the melanocytes situated in the basal layer of the epidermis. This differentiation generally comprises four different stages (I to IV) corresponding to the accumulation of the pigment, i.e. the melanin, within the melanosomes (cellular organelles for storing and transferring the melanin). Stage IV (the most strongly colored) is the final stage of the charging of the melanosomes with pigment, so these melanosomes are considered to be mature. It is also known that it is at this stage that the melanin contained in the melanosomes is transferred to the keratinocytes situated at a higher level in the epidermis, via the dendritic extensions of the melanocytes.

Description of the assay:

Normal human melanocytes, isolated in conventional manner in the course of a face-lift on a 50-year-old woman, are placed on day D=0 in complete M 199 culture medium (GIBCO) comprising 10% v/v of fetal calf serum and supplemented with conventional growth factors.

On day D=3, 10 μg/ml of extract $I_2$ of black horehound (ethyl acetate extract) of Example 2, solubilized in DMSO, are added to the culture medium.

On day D=6, the medium is renewed with a medium of identical composition which also contains 10 μg/ml of extract $I_2$.

On day D=9, the cells are included in EPON 812® resin (glycerol diglycidyl and triglycidyl ether) available from LADD, Vermont, USA. The blocks of resin are then cut into ultrafine sections by means of a microtome. The ultrastructure of the cells can thus be observed by transmission electron microscopy.

In a parallel procedure, a control culture of melanocytes was prepared from the same source and under the same conditions, except that no extract was added to the culture from day D=3, only DMSO being added at the same concentration, i.e. 0.1% by volume.

Observation by electron microscopy shows that the control culture exhibits mainly stage I and II melanosomes. Furthermore, in the melanocytes, the reticuloendothelial system and the Golgi apparatus display little activity.

By contrast, the treated culture exhibits numerous melanosomes which have reached stages III and IV in the majority of cells. The reticuloendothelial system and the Golgi apparatus of the cells, which is where tyrosinase synthesis and glycosylation and the formation of the melanin-secreting vesicles take place, are very developed and hence very active. These characteristics together indicate the existence of differentiated melanocytes, especially insofar as they possess numerous stage III and IV mature melanosomes.

Thus the demonstration of a mechanism of action of the extracts of black horehound makes it possible on the one hand to explain the activity of the compositions according to the invention which promote the pigmentation of the skin, and on the other hand to carry out a process for the cultivation of more highly differentiated melanocytes with melanosomes of greater maturity, it then being possible for these melanocytes to be used in grafts for treating certain pigmentation disorders such as vitiligo.

EXAMPLE 6

Demonstration of the inhibitory activity of the products of the invention on the accumulation of triglycerides in the adipocytes Triglycerides, which constitute an important energy reserve of the organism, are formed from glycerol and fatty acids in the intestinal wall, the liver and the adipose tissues.

Excesses of fat in the organism are thus associated directly with the accumulation of triglycerides in the adipocytes.

Furthermore, it is known that certain lines of fibroblasts in culture, in particular the 3T3-L1 line, are capable of differentiating into adipocytes when the culture conditions allow (for example according to the technique described by Teruo Kawada et al. in Comp. Biochem. Physiol. (1990) vol. 96A, N.2, pp. 323–326).

Thus, to demonstrate the inhibitory activity of the products of the invention on the accumulation of triglycerides in the adipocytes, a culture of this line was prepared under conditions which permitted their differentiation into adipocytes, in the presence of $^{14}C$-labeled glucose and in the presence or absence of a product according to the invention.

The glycerol utilized by the cells to synthesize the triglycerides originates indirectly from the glycolysis of glucose. Thus, under the conditions of the test performed, it will suffice to measure the radioactivity of the triglycerides extracted at the end of the experiment in order to assess the accumulation of triglycerides by the adipocytes.

On day D=0, Petri dishes of diameter 35 mm, containing 2 ml of a culture medium consisting of complete EMEM containing 10% v/v of fetal calf serum, are inoculated with $2 \times 10^5$ cells/dish of the 3T3-L1 line (available from ATCC, reference CCL 92-1).

On day D=1, the culture medium is replaced with that used on day D=0 to which the differentiating agents, namely 100 μg/ml of isobutylmethylxanthine (IBMX) and 0.1 μg/ml of dexamethasone, mitomycin C and $^{14}$C-glucose at a concentration of 0.5 µCi/ml have been added. This culture medium also contains the test products, with the exception of the medium corresponding to the control cultures.

On day D=7, the triglycerides present in the cultures are extracted with heptane. This is done by first removing the cells in culture from their dish in conventional manner by means of a trypsin solution. The resulting cell suspension is then lyzed by the addition of a sufficient amount of Dole's reagent (Dole V. P. et al., Journal of Biological Chemistry (1960) vol. 235, N.9, pp. 2595). Water and then heptane are subsequently added to the preparation to give two phases, the one aqueous and the other organic and consisting of heptane. The heptane phase, containing the triglycerides present in the culture, is then collected and its radioactivity is determined by liquid scintillation, for example by means of an apparatus of the KONTRON BETA V® type.

The measurement of the radioactivity of the extracts obtained from the cultures containing the product of the invention, compared with the measurement of the control cultures, therefore makes it possible to evaluate the inhibition of the accumulation of triglycerides, the latter being formed from the radioactive glucose not extracted by the heptane.

Thus the activity A of the products of the invention is calculated by means of the following formula:

$$A = \frac{R_t - R_p}{R_t} \times 100$$

$R_t$ being the radioactivity of the triglyceride extracts of the control cultures, expressed in cpm (counts per minute), and $R_p$ being the radioactivity of the cultures in the presence of the product according to the invention, also expressed in cpm.

The product of the invention forming the subject of the present assay consists of methanolic extract $I_1$ of black horehound obtained according to Example 1.

Table III below shows the results of the inhibitory activity of extract $I_1$ at two different concentration values in the cultures.

TABLE III

| $I_1$ (µg/ml) | Radioactivity R (cpm) | Activity A | Significance t |
|---|---|---|---|
| 50 | 14,199 ± 409 | 44.2% | S |
| 10 | 20,434 ± 907 | 19.8% | S |
| Control | 25,463 ± 1,890 | 0 | |

The significance of the results was calculated by the Student t test with $p<0.05$.

This Table clearly shows that the presence of extract $I_1$ according to the invention substantially and significantly inhibits the accumulation of triglycerides in adipocytes in culture.

The products of the invention can thus advantageously be used as the active principle in cosmetic or pharmaceutical compositions, especially dermatological compositions, for preventing or treating excesses of fat, in particular cellulitis.

Various Formulation Examples of cosmetic or pharmaceutical compositions, especially dermatological compositions, are now given below.

EXAMPLE 7.

| Lotion for promoting the pigmentation of the hair: | |
|---|---|
| extract $I_1$ (Example 1) | 0.15 g |
| propylene glycol | 5 g |
| Cremophor RH40 ® | 1 g |
| ethanol | 30 g |
| perfumed aqueous excipient qsp | 100 g |

The lotion is applied to the hair at a rate of 1 ml twice a day for 6 months to give a significant pigmentation effect.

EXAMPLE 8

| Gel for promoting tanning The gel is prepared from the following two phases A and B: | |
|---|---|
| 1) Phase A | |
| extract $I_2$ (Example 2) | 0.1 g |
| malyltyrosine | 2 g |
| propylene glycol | 4 g |
| glycerol | 0.5 g |
| Cremophor RH40 ® | 1 g |
| ethanol | 25 g |
| perfumed aqueous excipient qsp | 50 g |
| 2) Phase B | |
| 1.25% Carbopol 940 ® gel | 50 g |

Phase A is added gradually to phase B and the two are mixed with a propeller stirrer until dispersion is complete.

This gives a gel for promoting tanning of the skin, which can be applied before or during exposure to the sun.

EXAMPLE 9

| Slimming composition | |
|---|---|
| extract of black horehound according to the invention (Example 1) | 0.1 g |
| 96% alcohol | 32 g |
| Carbopol 941 ® | 2.5 g |
| aqueous excipient with preservative qsp | 100 g |

The extract of black horehound is first dissolved in the alcohol, after which the whole is incorporated into a gelled excipient containing the Carbopol.

This gives a slimming composition which can be applied to the areas to be treated.

What is claimed is:

1. A method of promoting pigmentation of skin or hair, comprising applying to areas of the skin, scalp or hair of a person in need thereof, an effective amount of at least one solvent extract of black horehound to increase the pigmentation of said areas, to restore normal pigmentation of said areas or to prevent or slow down the appearance of white or grey hair said solvent being selected from the group consisting of an alcohol, an alcohol-water mixture, a $C_1$–$C_2$ chlorinated solvent, an organic ester, an aromatic hydrocarbon, an halogenated aliphatic hydrocarbon, an halogenated aromatic hydrocarbon, a dialkylether, a dialkyl ketone, a carboxylic acid, dimethylformamide, dioxane, tetrahydrofuran, dimethyl sulfoxide and super-critical carbon dioxide gas.

2. The method of claim 1, wherein said black horehound is selected from the group consisting of Ballota nigra, Ballota lanata and Ballota suavelens.

3. The method of claim 1, wherein said extract of black horehound is an extract selected from the group consisting of an extract of the whole plant, an extract of the aerial part, an extract of the stem, and an extract of the leaves.

4. The method of claim 1, wherein said extract of black horehound is an extract obtained by at least one extraction step with an organic solvent selected from the group consisting of an alcohol, from 1 to 4 carbon atoms, a water/alcohol admixture, a chlorinated solvent from 1 to 2 carbon atoms, and an organic ester from 3 to 6 carbon atoms.

5. The method of claim 4, wherein said alcohol is selected from the group consisting of methanol, ethanol and propanol.

6. The method of claim 4, wherein said chlorinated solvent is selected from the group consisting of chloroform and dichloromethane.

7. The method of claim 4, wherein said organic ester is ethylacetate.

8. The method of claim 1, wherein said extract of black horehound is applied at a concentration, expressed by dry weight, ranging between 0.0001% and 5% by weight, based on the total weight of the composition.

9. The method of claim 1, wherein said extract of black horehound is applied at a concentration, expressed by dry weight, ranging between 0.01% and 0.5% by weight, based on the total weight of the composition.

10. The method of claim 1, wherein said extract of black horehound is present in a composition further comprising a xanthine.

11. The method of claim 10, wherein said xanthine is selected from the group consisting of 1-methylxanthine, 3-methylxanthine, 3-isobutylmethylxanthine and theophylline.

12. The method of claim 10, wherein said xanthine is present at a concentration ranging between 0.001% and 2% by weight, based on the total weight of the composition.

13. The method of claim 10, wherein said xanthine is present at a concentration ranging between 0.01% and 0.5% by weight, based on the total weight of the composition.

14. The method of claim 1, wherein said extract of black horehound is present in a composition further comprising a tyrosine component selected from the group consisting of tyrosine N-malyltyrosine and a tyrosine ester.

15. The method of claim 14, wherein said tyrosine component is at a concentration ranging between 0.001% and 10% by weight, based on the total weight of the composition.

16. The method of claim 14, wherein said tyrosine ester is glucose tyrosinate.

17. The method of claim 1, wherein said extract of black horehound is present in a composition further comprising another active substance selected from the group consisting of vitamins, quinine, rubefacients, a papilla fibroblast culture supernatant, a keratin hydrolyzate; a trace element, a 5-$\alpha$-reductase element, a 5-$\alpha$reductase inhibitor, cyproterone acetate, minoxidil, azelaic acid, a 1,4-methyl-4-azasteroid, and an extract of Serenoa repens.

18. The method of claim 17, wherein said vitamin is belonging to the B vitamin group.

19. The method of claim 17, wherein said rubefacient is methylnicotinate.

20. The method of claim 17, wherein said trace element is selected from the group consisting of zinc, selenium and copper.

21. The method of claim 17, wherein said 5-$\alpha$-reductase inhibitor is progesterone.

22. The method of claim 17, wherein said 1,4-methyl-4-azasteroid is 17-$\beta$-N,N-diethylcarbamoyl-4-methyl-4-aza-5-$\alpha$-androstan-3-one.

23. The method of claim 1, wherein said extract of black horehound is present in a composition further comprising at least one active substance selected from the group consisting of a xanthine, an extract of ivy and an extract of Coleus.

24. The method of claim 23, wherein said xanthine is caffeine.

25. The method of claim 23, wherein said extract of Coleus is an extract of Coleus forskohlii.

26. The method of claim 1, wherein said extract of black horehound is applied topically and is present in a composition further comprising an agent promoting penetration and diffusion in the skin structure.

27. The method of claim 26, wherein said agent promoting penetration and diffusion in the skin structure is selected from the group consisting of ethyl alcohol, a glycol, oleic acid, laurocapram and an essential oil.

28. The method of claim 27, wherein said glycol is selected from the group consisting of glycerol and propylene glycol.

29. The method of claim 27, wherein said essential oil is selected from the group consisting of menthol and eucalyptol.

30. The method of claim 1, wherein said extract of black horehound is applied topically and is present in a composition further comprising an agent promoting penetration and diffusion in the skin structure.

31. The method of claim 30, wherein said agent promoting penetration and diffusion in the skin structure is selected from the group consisting of ethyl alcohol, a glycol, oleic acid, laurocapram and an essential oil.

32. The method of claim 31, wherein said glycol is selected from the group consisting of glycerol and propylene glycol.

33. The method of claim 27, wherein said essential oil is selected from the group consisting of methanol and eucalyptol.

34. The method of claim 1, wherein said extract of black horehound is present in a composition further comprising hydrated lipidic lamellar phases or liposomes.

35. A pharmaceutical or cosmetic composition formulated for topical administration to the skin, scalp or hair, comprising a pharmaceutically or cosmetically effective amount of a solvent extract of black horehound in a pharmaceutically or cosmetically acceptable excipient adapted for said topical administration to the skin or scalp, said solvent being selected from the group consisting of an alcohol, an alcohol-water mixture, a $C_1$-$C_2$ chlorinated solvent, an organic ester, an aromatic hydrocarbon, an halogenated aliphatic hydrocarbon, an halogenated aromatic hydrocarbon, a dialkylether, a dialkyl ketone, a carboxylic acid, dimethylformamide, dioxane, tetrahydrofuran, dimethyl sulfoxide and supercritical carbon dioxide gas.

36. The composition of claim 35, wherein the black horehound is selected from the group consisting of Ballota nigra, Ballota lanata and Ballota suavelens.

37. The composition of claim 35, wherein said extract of black horehound is selected from the group consisting of an extract of the whole plant, an extract of the aerial part, an extract of the stem and an extract of the leaves.

38. The composition of claim 35, wherein said extract of black horehound is an extract obtained by at least one extraction step with an organic solvent selected from the group consisting of an alcohol from 1 to 4 carbon atoms, a water/alcohol admixture, a chlorinated solvent from 1 to 2 carbon atoms, and an organic ester from 3 to 6 carbon atoms.

39. The composition of claim 35, wherein said extract of black horehound is present in a composition at a concentration, expressed by dry weight, ranging between 0.0001% and 5% by weight, based on the total weight of the composition.

40. The composition of claim 35, wherein said extract of black horehound is present in a composition at a concentration, expressed by dry weight, ranging between 0.01% and 0.5% by weight, based on the total weight of the composition.

41. The composition of claim 35, further comprising at least another active substance selected from the group consisting of a xanthine, a tyrosine component, an extract of ivy, an extract of Coleus, vitamins, quinine, rubefacients, a papilla fibroblast culture supernatant, a keratin hydrolyzate; trace elements, 5-α-reductase inhibitors, cyproterone acetate, minoxidil, azelaic acid, a 1,4-methyl-4-azasteroid, and an extract of Serenoa repens.

42. The composition of claim 41, wherein said xanthine is selected from the group consisting of 1-methylxanthine, 3-methylxanthine, 3-isobutylmethylxanthine, theophylline and caffeine.

43. The composition of claim 41, further comprising a tyrosine component selected from the group consisting of tyrosine, N-malyltyrosine and tyrosine ester.

44. The composition of claim 43, wherein said tyrosine component is present at a concentration ranging between 0.001% and 10% by weight, based on the total weight of the composition.

45. The composition of claim 41, wherein said vitamin belongs to the B vitamin group.

46. The composition of claim 41, wherein said rubefacient is methyl nicotinate.

47. The method of claim 41, wherein said trace element is selected from the group consisting of zinc, selenium and copper.

48. The composition of claim 41, wherein said 5-α-reductase inhibitor is progesterone.

49. The composition of claim 41, wherein said 1,4-methyl-4-azasteroid is 17-β-N,N-diethylcarbamoyl-4-methyl-4-aza-5-α-androstan-3-one.

50. The composition of claim 41, wherein said extract of Coleus is an extract of Coleus forskohlii.

51. The composition of claim 35, further comprising an agent promoting penetration and diffusion in the skin structures.

52. The composition of claim 51, wherein said agent promoting penetration and diffusion is selected from the group consisting of ethyl alcohol, a glycol, oleic acid, laurocapram and an essential oil.

53. The composition of claim 52, wherein said glycol is glycerol or propylene glycol.

54. The composition of claim 52, wherein said essential oil is menthol or eucalyptol.

55. The composition of claim 44, wherein said xanthine is present at a concentration ranging between 0.001% and 2% by weight, based on the total weight of the composition.

56. The composition of claim 35, wherein said topical composition is selected from the group consisting of a cream, a gel, a milk and a lotion.

57. The composition of claim 35, further comprising hydrated lipidic lamellar phases and liposomes.

58. A composition comprising 0.001% to 5% by weight, expressed by dry weight, based on the total weight of the composition, of a solvent extract of black horehound admixed with an excipient which is adapted for a topical administration of said composition to the skin, scalp or hair, said solvent being selected from the group consisting of an alcohol, an alcohol-water mixture, a $C_1$–$C_2$ chlorinated solvent, an organic ester, an aromatic hydrocarbon, an halogenated aliphatic hydrocarbon, an halogenated aromatic hydrocarbon, a dialkylether, a dialkyl ketone, a carboxylic acid, dimethylformamide, dioxane, tetrahydrofuran, dimethyl sulfoxide and super-critical carbon dioxide gas.

59. The composition of claim 58, wherein the black horehound is selected from the group consisting of Ballota nigra, Ballota lanata and Ballota suavelens.

60. A composition comprising from 0.01% to 5% by weight, expressed by dry weight based on the total weight of the composition of a solvent extract of black horehound admixed with an excipient formulated for a topical administration to the skin, scalp or hair, said solvent being selected from the group consisting of an alcohol, an alcohol-water mixture, a $C_1$–$C_2$ chlorinated solvent, an organic ester, an aromatic hydrocarbon, an halogenated aliphatic hydrocarbon, an halogenated aromatic hydrocarbon, a dialkylether, a dialkyl ketone, a carboxylic acid, dimethylformamide, dioxane, tetrahydrofuran, dimethyl sulfoxide and supercritical carbon dioxide gas.

61. A composition comprising from 0.01% to 0.5% by weight, expressed by dry weight based on the total weight of the composition of a solvent extract of black horehound admixed with an excipient formulated for a topical administration to the skin, scalp or hair, said solvent being selected from the group consisting of an alcohol, an alcohol-water mixture, a $C_1$–$C_2$ chlorinated solvent, an organic ester, an aromatic hydrocarbon, an halogenated aliphatic hydrocarbon, an halogenated aromatic hydrocarbon, a dialkylether, a dialkyl ketone, a carboxylic acid, dimethylformamide, dioxane, tetrahydrofuran, dimethyl sulfoxide and supercritical carbon dioxide gas.

62. A cosmetic composition for promoting pigmentation of the skin or hair of a person, formulated for topical administration to the skin, scalp or hair, comprising a pigmenting effective amount of at least one solvent extract of black horehound in a cosmetically acceptable excipient adapted for topical application to the skin, scalp or hair.

* * * * *